(12) United States Patent
Varghese et al.

(10) Patent No.: US 10,413,360 B2
(45) Date of Patent: Sep. 17, 2019

(54) SKIN TREATMENT DEVICE FOR MULTI-PHOTON BASED SKIN TREATMENT

(71) Applicant: KONINKLIJKE PHILIPS N.V., Eindhoven (NL)

(72) Inventors: Babu Varghese, Eindhoven (NL); Rieko Verhagen, Eindhoven (NL); Martin Jurna, Eindhoven (NL); Jonathan Alambra Palero, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 652 days.

(21) Appl. No.: 15/030,385

(22) PCT Filed: Oct. 31, 2014

(86) PCT No.: PCT/EP2014/073407
§ 371 (c)(1),
(2) Date: Apr. 19, 2016

(87) PCT Pub. No.: WO2015/063245
PCT Pub. Date: May 7, 2015

(65) Prior Publication Data
US 2016/0249982 A1 Sep. 1, 2016

(30) Foreign Application Priority Data

Oct. 31, 2013 (EP) ..................................... 13191002

(51) Int. Cl.
*A61B 18/20* (2006.01)
*A61B 18/00* (2006.01)
*A61N 5/073* (2006.01)

(52) U.S. Cl.
CPC ............ *A61B 18/203* (2013.01); *A61B 18/20* (2013.01); *A61B 2018/0047* (2013.01); *A61B 2018/00696* (2013.01); *A61N 2005/073* (2013.01)

(58) Field of Classification Search
CPC ................ A61B 18/20; A61B 18/203; A61B 2018/0047; A61B 2018/00696; A61B 2005/073; A61N 2005/073
(Continued)

(56) References Cited

U.S. PATENT DOCUMENTS 5,980,513 A * 11/1999 Frey ................... A61B 3/113
351/209
8,821,482 B2 9/2014 Verhagen
(Continued)

FOREIGN PATENT DOCUMENTS

WO 2006101736 A1 9/2006
WO 2008001284 A2 1/2008
(Continued)

OTHER PUBLICATIONS

J. Noack and A. Vogel, "Laser-Induced Plasma Formation in Water at Nanosecond to Femtosecond Time Scales: Calculation of Thresholds, Absorption Coefficients, and Energy Density," IEEE J. Quantum Electron. 35(1999).
(Continued)

*Primary Examiner* — Michael W Kahelin
*Assistant Examiner* — Wynn V Huh

(57) ABSTRACT

The invention provides a non-invasive skin treatment device (100) comprising: a light source (10) constructed and configured for generating linearly polarized probe light (12) and linearly polarized treatment light (22), a polarization modulator (30) constructed and configured for controlling a polarization direction of the probe light and a polarization
(Continued)

direction of the treatment light, a polarization sensitive sensor (40) constructed and configured for sensing a level of depolarization of the probe light by sensing an intensity of back-scattered probe light (42) from the target position (210) in a predefined polarization direction of the polarization sensitive sensor, and a controller (60) being configured for scanning the polarization direction of the probe light over a predefined range while receiving the measurement signal (Sm) and for selecting an optimum polarization (P1) direction for which the depolarization of the probe light is at a minimum. The invention further provides a computer program product for controlling the skin treatment device.

13 Claims, 6 Drawing Sheets

(58) Field of Classification Search
USPC .............................................................. 606/9
See application file for complete search history.

(56) References Cited

U.S. PATENT DOCUMENTS

| 9,022,037 | B2* | 5/2015 | Delfyett | A61B 18/20 |
| | | | | 128/898 |
| 2006/0241585 | A1 | 10/2006 | Silberberg | |
| 2007/0021807 | A1 | 1/2007 | Kurtz | |
| 2008/0114340 | A1 | 5/2008 | Fox | |
| 2010/0082019 | A1 | 4/2010 | Neev | |

FOREIGN PATENT DOCUMENTS

| WO | 2013027142 A2 | 2/2013 |
| WO | 2013128330 A1 | 9/2013 |

OTHER PUBLICATIONS

E. W. B. Richards, "Electromagnetic diffraction in optical system II. Structure of the imaged field in an aplanatic system," Proc. R. Soc. Lond. A (1959).

L. Habbema, R. Verhagen, R. Van Hal, Y. Liu, B. Varghese, "Minimally invasive non-thermal laser technology using laser-induced optical breakdown for skin rejuvenation", Journal of Biophotonics, (2011).

Babu Varghese and Rieko Verhagen, Removal of tattoos and pigmented lesions using plasma mediated multi-photon ionization created by focussed pico-second laser pulses, ID 2011ID08029.

* cited by examiner

SKIN TREATMENT DEVICE FOR MULTI-PHOTON BASED SKIN TREATMENT

This application is the U.S. National Phase application under 35 U.S.C. § 371 of International Application No. PCT/EP2014/073407, filed on Oct. 31, 2014, which claims the benefit of International Application No. 13191002.8 filed on Oct. 31, 2013. These applications are hereby incorporated by reference herein.

FIELD OF THE INVENTION

The invention generally relates to the treatment of skin using laser light, and more particularly to a skin treatment device and computer program product for controlling the skin treatment device.

BACKGROUND OF THE INVENTION

The desire to maintain a youthful appearance by preventing or reducing wrinkles in the skin is an important issue in human society. Many techniques have been designed to achieve the above issue. One of the techniques, known from the published international patent application WO 2008/001284 A2, is to create a focal spot in a dermis layer of the skin to be treated. Said WO application discloses a skin treatment device with a laser source and focusing optics, wherein the power of the laser is selected such that Laser Induced Optical Breakdown (LIOB) affects the skin in order to stimulate re-growth of skin tissue and reduce wrinkles. This LIOB is based on strong non-linear absorption of the laser light by the skin tissue, which occurs above a certain threshold value for the power density of the laser light. This strong absorption causes localized plasma that is able to damage or even remove tissue at the location of said plasma. This is caused by secondary, primarily mechanical effects such as rapid expansion of the generated plasma. This effect is very local, because below the threshold there is zero or very little linear and non-linear absorption, while above the threshold plasma is generated, which even more strongly absorbs the radiation. In other words, effects such as LIOB only occur at the focal spot, while above and below the focal spot no or very much weaker effects occur. This means that for example the epidermis may easily be safeguarded against undesired effects or damage.

The focal point is created at a fixed treatment depth, somewhere between 0 and 2.0 mm. This depth is selected based on the typical composition of human skin. In some cases, however, the optimum treatment depth may be different. The optimum treatment depth depends on, e.g., the thickness of the stratum corneum and the epidermis.

In addition to LIOB, also other multi-photon absorption processes such as second harmonic generation, third harmonic generation and other higher harmonic generation processes may be used to image and modify tissue to stimulate re-growth of the modified tissue to rejuvenate the tissue and reduce wrinkles Laser skin ablation through multi-photon ionization (e.g.: laser induced optical breakdown) requires high light intensities in the order of $10^{13}$ W/cm$^2$. Due to a very high photon flux (typically $>10^{31}$ cm$^{-2}$s$^{-1}$), multiple (N) photons with energy of hv at a wavelength of $\lambda$ behave like a photon of energy Nhv interacting with an electron to free it from the valence band. This requires that the total energy of the absorbed photons is greater than the ionization potential (Nhv>$\Delta$). The generation of this seed electron by ionization requires multiple photons (N) having the same polarization confined in space (focal volume) and time (~femto seconds) with a total energy exceeding the ionization potential (Nhv>$\Delta$) of the material. Multi-photon ionization deep inside skin is challenging to achieve.

SUMMARY OF THE INVENTION

An object of the invention is to provide a non-invasive skin treatment device for multi-photon processes in which the multi-photon process is produced at relatively low light intensity.

The object is achieved according to the invention by a skin treatment device comprising:
a light source constructed and configured for generating linearly polarized probe light and linearly polarized treatment light,
a polarization modulator constructed and configured for controlling a polarization direction of the probe light and a polarization direction of the treatment light,
a polarization sensitive sensor constructed and configured for sensing a level of depolarization of the probe light by sensing an intensity of back-scattered light from the target position at a predefined polarization direction of the polarization sensitive sensor, and
a controller constructed and configured for receiving a measurement signal from the sensor and providing a control signal to the polarization modulator and the light source, the controller being configured for controlling the polarization modulator such as to scan the polarization direction of the probe light over a predefined range of polarization directions while receiving the measurement signal and for selecting an optimum polarization direction for which the level of depolarization of the probe light is at a minimum.

The invention is based on the insight that the intensity threshold to create multi-photon ionization is a function of both medium characteristics and beam characteristics. The medium characteristics may, for example, be ionization energy or impurity levels, and the beam characteristics may, for example, be wavelength used, pulse width, spot size, and polarization. To generate a seed electron for the multi-photon ionization process, multiple photons having the same polarization direction are necessary at the target position. When polarized light is focused inside turbid media like skin, the fraction of photons having the same polarization is significantly reduced. This is caused by the change in polarization due to high NA focusing, multiple scattering and skin birefringence. To compensate for the reduction in the number of photons with the same polarization available for multi-photon ionization in the focal volume, the known solution is to increase simply the number of photons. In the known skin treatment devices, this leads to a high intensity threshold for ionization and possible collateral damage of the surrounding tissue. The inventors have found that for a specific polarization direction also indicated as the optimum polarization direction the depolarization effect of the skin at a specific skin position is at a minimum. This results in a minimum power level of the treatment light required to generate multi-photon ionization. The inventors have also found that this optimum polarization direction may differ at different locations in the skin tissue. Therefore, the skin treatment device according to the invention comprises a polarization modulator which is controlled by a control unit to locally adapt the polarization direction of the emitted linearly polarized probe light to find the optimum polarization direction. Subsequently initiating the emission of treatment light with a polarization direction corresponding to this optimum polarization direction for the current target position will result in the generation of the multi-photon ionization process at a minimum treatment light intensity. As a result, damage to the tissue surrounding the target position is minimized. A further benefit of this local selection and adaption of the polarization direction of the linearly polarized probe light (and treatment light) by the polarization modulator is that it may also reduce the requirements imposed on the light source for generating the polarized treatment light. This would subsequently also reduce the overall cost of the skin treatment device according to the invention.

The controller in the skin treatment device according to the invention is constructed and configured for scanning the polarization direction of the probe light over a predefined range while receiving the measurement signal. This predefined range may, for example, be a range of ninety degrees, in which, for example, the polarization direction of the probe light at the end of the scan is perpendicular to the polarization direction of the probe light at the start of the scan. Alternatively, the predefined range may be more than ninety degrees.

In an embodiment of the skin treatment device, the controller is constructed and configured for controlling the polarization modulator such as to set the selected optimum polarization direction as the polarization direction of the treatment light at the target position for generating the multi-photon ionization process. As indicated hereinbefore, when the optimum polarization direction is found after scanning the polarization direction of the probe light, the controller sets this optimum polarization direction as the polarization direction of the treatment light to be able to initiate the multi-photon ionization process at a minimum treatment light intensity for the current target position.

The polarization modulator may comprise a single modulation element which adapts the polarization direction of both the probe light and the treatment light. Alternatively, the polarization modulator may comprise two modulation elements, one modulation element for adapting the polarization direction of the probe light and another modulation element for adapting the polarization direction of the treatment light.

In an embodiment of the skin treatment device, the skin treatment device is configured and constructed to maintain the predefined polarization direction of the polarization sensitive sensor parallel to the polarization direction of the probe light during the scanning of the polarization direction of the probe light. In such a configuration, the optimum polarization direction is selected to be the probe light polarization direction for which the intensity of the sensed back-scattered probe light is at a maximum seen over the predefined range of polarization directions of the probe light. Some of the probe light will scatter back towards the polarization sensitive sensor. When the depolarization is at a minimum, a minimal part of the probe light (and of the back-scattered probe light) will have changed polarization and thus the intensity measured at the polarization sensitive sensor will be at a maximum. With regard to this embodiment, it is noted that the polarization direction of the probe light relates to the polarization direction of the probe light to which the skin tissue is actually exposed, i.e. the polarization direction of the probe light after having passed the polarization modulator. Consequently, the predefined polarization direction of the polarization sensitive sensor relates to a predefined polarization direction of the back-scattered probe light as emitted by the skin at the position of the skin surface.

In an embodiment of the skin treatment device, the skin treatment device is configured and constructed to maintain the predefined polarization direction of the polarization sensitive sensor perpendicular to the polarization direction of the probe light during the scanning of the polarization direction of the probe light. In such a configuration of the polarization sensitive sensor, the optimum polarization direction is selected as the probe light polarization direction for which the intensity of the sensed back-scattered probe light is at a minimum, seen over the predefined range of polarization directions of the probe light. Again, some of the probe light will scatter back towards the polarization sensitive sensor. When the polarization direction of the polarization sensitive sensor remains perpendicular to the polarization direction of the probe light during the scanning of the probe light, the polarization sensitive sensor only senses the back-scattered probe light which has changed polarization direction due to the depolarization effect of the skin tissue. When the depolarization is at a minimum, a minimal part of the probe light (and of the back-scattered probe light) will have changed polarization and thus the intensity measured at the polarization sensitive sensor will be at a minimum. Because the sensing of a minimum usually is more reliable and can typically be done more accurately, the embodiment in which the polarization direction of the polarization sensitive sensor is maintained perpendicular to the polarization direction of the probe light is preferred. With regard to this embodiment, it is noted that the polarization direction of the probe light relates to the polarization direction of the probe light to which the skin tissue is actually exposed, i.e. the polarization direction of the probe light after having passed the polarization modulator. Consequently, the predefined polarization direction of the polarization sensitive sensor relates to a predefined polarization direction of the back-scattered probe light as emitted by the skin at the position of the skin surface.

In an embodiment of the skin treatment device, the polarization modulator is positioned between the target position and the polarization sensitive sensor such that the back-scattered probe light is transmitted to the polarization sensitive sensor via the polarization modulator. In such a configuration, the back-scattered probe light is measured via the same polarization modulator as that used to modulate the probe light during the scanning of the probe light over the predefined range. The polarization sensitive sensor only needs to be sensitive to a single fixed polarization direction to ensure that the correct polarization direction for the measurement of the back-scattered probe light is maintained. While the polarization direction of the probe light is being modulated over the predefined range during the scanning, the back-scattered probe light will automatically be "de-modulated" before being measured by the polarization sensitive sensor. Using, for example, a fixed polarizing filter in front of a light intensity sensor will automatically ensure that the measurement is performed in the correct polarization direction. Depending on the required configuration, the fixed polarizing filter may be perpendicular to the probe light as emitted by the light source, or may be parallel to the probe light as emitted by the light source.

It may also be advantageous to provide the skin treatment device, wherein the skin treatment device comprises an optical system for focusing the probe light and/or the treatment light to the target position inside the skin tissue, and wherein the controller is connected to the optical system and is configured and constructed for re-initiating the scanning of the polarization direction of the probe light over the predefined range for re-selecting the optimum polarization direction in response to a change in depth of the target position inside the skin tissue relative to a skin surface. As indicated hereinbefore, the optimum polarization direction of the linearly polarized probe light or linearly polarized treatment light may change for different target positions inside the skin tissue. When the depth of the target position is changed—for example by an operator of the skin treatment device—the optimum polarization direction of the previous target position may no longer be optimal for the changed current target position. To ensure that the intensity of the treatment light used for multi-photon ionization inside the skin tissue remains at a minimum, the skin treatment device is configured to re-adjust the optimum polarization direction for the new target position at the new treatment depth. In such an embodiment, the skin treatment device according to the invention may comprise a further sensor for sensing a change in depth of the target position and provides such depth information as a depth signal to the controller. The controller may, for example, use such a depth signal as a trigger to re-adjust the optimum polarization direction.

In an embodiment of the skin treatment device, the controller is connected to a motion sensor for sensing motion of the skin treatment device parallel to the skin surface, and wherein the controller is configured and constructed for re-initiating the scanning of the polarization direction of the probe light over the predefined range for re-selecting the optimum polarization direction in response to a change in position of the skin treatment device along the skin surface. Similar to the change in depth of the target position, also a relocation of the skin treatment device along the skin surface may result in a change of the optimum polarization direction of the emitted linearly polarized probe light or treatment light at this changed position. Therefore, the controller may be configured to receive a motion signal from the motion sensor and—in response to receiving such a motion signal—the controller may use this motion signal as a trigger to re-adjust the optimum polarization direction, for example, before applying the multi-photon ionization treatment at the relocated target position.

In an embodiment of the skin treatment device, a probe light power level is below a treatment light power level required for the multi-photon process. When using probe light which has a lower power level than the treatment light to find the optimum polarization direction, the chances of damaging the skin while trying to find the optimum polarization direction are significantly reduced. Still, using this probe light having the lower power level allows selecting the optimum polarization direction of the current target position. Furthermore, the power requirements of such a probe light are significantly lower than the power required to generate the multi-photon ionization process. Consequently, by using probe light when scanning the polarization modulator to find the minimum depolarization, the overall power requirements of the skin treatment device are reduced. Especially in an embodiment in which the skin treatment device may be battery-operated, such a reduction in overall power requirements may be important.

In an embodiment of the skin treatment device, the light source comprises a probe light emitter for generating the linearly polarized probe light, and comprises a treatment light emitter for generating the linearly polarized treatment light. A benefit of such an embodiment is that both the probe light emitter and the treatment light emitter may each be specifically configured to emit their individually required power levels, which may reduce the overall requirements of the individual light emitters. Furthermore, a power level adjustment circuit, which could be required when only a single light emitter were present, may be omitted.

Alternatively, the light source in the skin treatment device according to the invention may have the single light emitter which may, for example, be configured to switch between different intensity levels for emitting the probe light or the treatment light.

In an embodiment of the skin treatment device, the skin treatment device comprises a further sensor for sensing an occurrence of the multi-photon process at the target position. Although the optimum polarization direction may be selected to ensure that the multi-photon ionization is carried out at the target position at the minimum light intensity, the minimum light intensity required at different target positions may still differ as already indicated. For example, when the depth of the target position inside the skin tissue is reduced, the de-polarization effect of the skin typically decreases because the light has to travel through less skin tissue. In such a situation, the intensity of the treatment light power level may be further reduced at this specific target position. Alternatively, if the multi-photon ionization treatment at a specific target position has to be performed at an increased depth, the optimum polarization direction may need to be adjusted due to the different target position, but also the light power level of the overall treatment may need to increase due to the increased depth inside the skin tissue (due to the increased path through the skin tissue, causing an increased depolarization effect despite the use of the optimum polarization). Therefore, in a further embodiment of the skin treatment device, the controller is connected to the further sensor for sensing the occurrence of the multi-photon process when the target position is exposed to the linearly polarized treatment light. When no multi-photon process is sensed, the controller may, for example, be configured to adjust a power level of the linearly polarized treatment light or reduce a depth of the target position inside the skin tissue relative to the skin surface. The further sensor for sensing the occurrence of the multi-photon process at the target position may be selected from a list comprising: photodetector, grating in combination with a CCD camera, and an acoustic sensor. The photodetector may comprise a photodiode, a photomultiplier tube, or a photon counter.

The multi-photon process may, for example, be light induced optical breakdown.

It may also be advantageous to provide the skin treatment device, wherein the target position is disposed in a dermis layer of the skin to be treated. For example, the target position is between 0.2 and 2 mm below the skin surface, or the target position is between 0.5 and 1.5 mm below the skin surface.

The object of the invention is also achieved by a computer program product for controlling the skin treatment device according to the invention, wherein the computer program controls the controller of the skin treatment device for performing the steps of:

generating and emitting the linearly polarized probe light towards the target position in skin tissue, using the light source, scanning the polarization direction of the probe light over the predefined range, using the polarization modulator, while receiving a measurement signal from the polarization sensitive sensor, and selecting the optimum polarization direction for which the depolarization of the probe light is at a minimum.

In an embodiment of the computer program product, the computer program further controls the controller for performing the steps of:

setting the selected optimum polarization direction as the polarization direction of the treatment light at the target position, using the polarization modulator, and generating and emitting the linearly polarized treatment light towards the target position, using the light source for generating the multi-photon ionization process.

It should be noted that items which have the same reference numbers in different Figures have the same structural features and the same functions, or constitute the same signals. Where the function and/or structure of such an item have been explained, there is no necessity for repeated explanation thereof in the detailed description.

DETAILED DESCRIPTION OF EMBODIMENTS

Figure 1A:
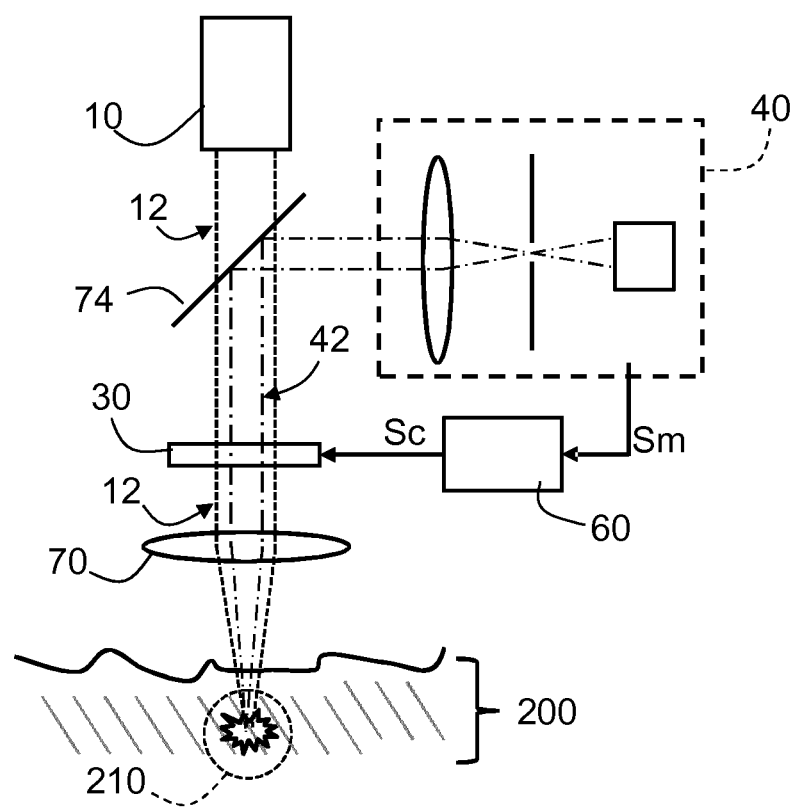
FIGS. 1A and 1B diagrammatically show a first embodiment of the skin treatment device according to the invention, FIGS. 2A and 2B diagrammatically show a second embodiment of the skin treatment device according to the invention, FIG. 3 diagrammatically shows a measurement signal measured by the sensor when changing the polarization direction of the emitted linearly polarized light.
Figure 1B:
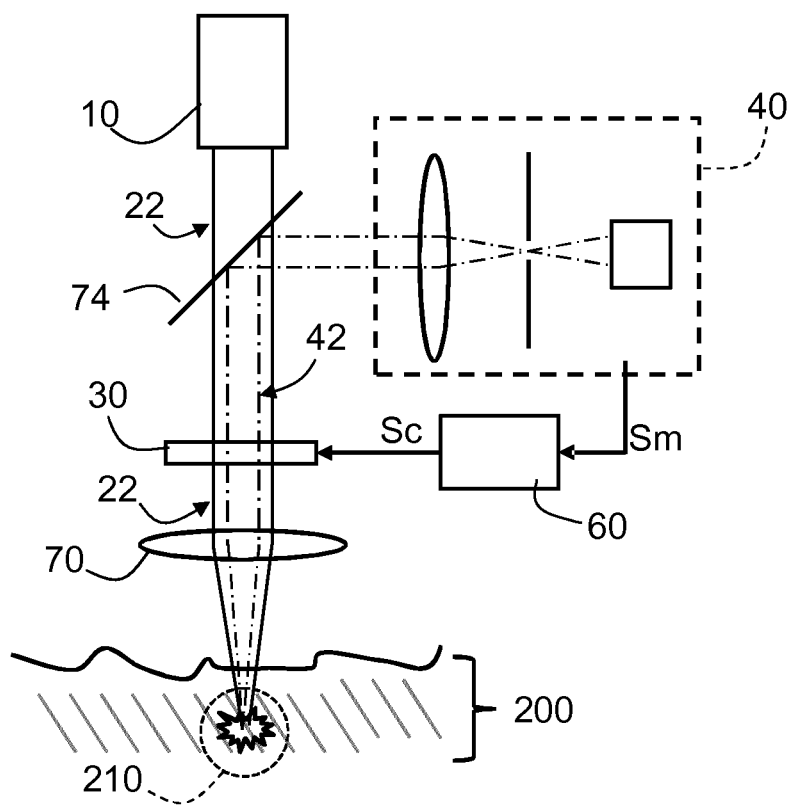

FIGS. 1A and 1B diagrammatically show a first embodiment of the skin treatment device 100 according to the invention. The skin treatment device 100 comprises a light source 10 constructed and configured for generating linearly polarized probe light 12 and linearly polarized treatment light 22 (see FIG. 1B). The skin treatment device 100 further comprises a polarization modulator 30 for controlling a polarization direction of the linearly polarized probe light 12 received from the light source 10, which light is emitted and focused using an optical system 70 toward the target position 210 inside the skin tissue 200. The skin treatment device 100 also comprises a polarization sensitive sensor 40 for sensing an intensity of the back-scattered probe light 42 from the target position 210. The polarization sensitive sensor 40 is configured for sensing a level of depolarization of the probe light 12 by sensing an intensity of back-scattered probe light 42 from the target position 210 in a predefined polarization direction of the polarization sensitive sensor 40. The back-scattered probe light 42 may, for example, be redirected to the polarization sensitive sensor 40, using a semi-transparent mirror 74. The skin treatment device 100 comprises a controller 60 configured and constructed for scanning the polarization direction of the probe light 12 over a predefined range while receiving a measurement signal Sm from the polarization sensitive sensor 40. The controller 60 is further configured for selecting an optimum polarization direction P1 (see FIG. 3) for which the depolarization of the probe light 12 is at a minimum for the current target position 210. Subsequently, this optimum polarization direction P1 is used as polarization direction of the treatment light 22 (see FIG. 1B) for generating the multi-photon ionization process at the target position 210. Using this optimum polarization direction P1 for the treatment light 22 will ensure that the power level required for the multi-photon ionization process at the current target location 210 is at a minimum.

The inventors have found that the intensity threshold to create multi-photon ionization is a function of both medium characteristics and beam characteristics. The current invention especially focuses on the influence of the polarization of the treatment light 22 on the multi-photon ionization. When polarized light is focused inside turbid media like skin tissue 200, the fraction of polarization-preserving photons having the same polarization is significantly reduced by the use of high NA focusing, multiple scattering and skin birefringence. However, in order to be able to generate multi-photon ionization, a specific density of photons having the same polarization direction is required at the target position 210. To compensate for the reduction in the number of photons with the same polarization available for multi-photon ionization in the focal volume, the known solution is to increase the number of photons, which leads to a relatively high intensity threshold for multi-photon ionization and possible collateral damage of the surrounding skin tissue 200. The inventors have found that for a specific polarization direction, the depolarization effect of the skin tissue 200 at a specific target position 210 is at a minimum, which results in a minimum power of the emitted linearly polarized treatment light 22 which may still be sufficient to generate multi-photon ionization. The inventors have also found that this specific polarization direction (indicated as the optimum polarization direction P1) may differ at different locations inside the skin tissue 200. Therefore, the skin treatment device 100 according to the invention comprises a polarization modulator 30 which is controlled by a control unit 60 to locally adapt the polarization direction of the emitted linearly polarized treatment light 22 such that the multi-photon polarization occurs at the minimum light intensity. As a result, damage to the skin tissue 200 surrounding the target position 210 may be minimized. A further benefit of this local adaption of the polarization direction of the emitted linearly polarized treatment light 22 by the polarization modulator 30 is that it may also reduce the requirements to be met by the light source 10 for generating the linearly polarized treatment light 22 and consequently may reduce the overall cost of such a skin treatment device 100.

The polarization sensitive sensor 40 may sense the back-scattered probe light 42 in a predefined polarization direction, for example, a polarization direction perpendicular to the linearly polarized probe light 12. While scanning the polarization direction of the probe light 12, also the predefined polarization direction of the polarization sensitive sensor 40 has to be scanned to ensure that the predefined polarization direction of the polarization sensitive sensor 40 remains perpendicular to the linearly polarized probe light 12. In such a configuration, the intensity of the back-scattered probe light 42 is at a minimum when the depolarization of the probe light 12 at the target location is at a minimum.

Alternatively, the predefined polarization direction of the polarization sensitive sensor 40 may be parallel to the linearly polarized probe light 12. Also in this case, while scanning the polarization direction of the probe light 12, the predefined polarization direction of the polarization sensitive sensor 40 has to be scanned to ensure that the predefined polarization direction of the polarization sensitive sensor 40 remains parallel to the linearly polarized probe light 12. In such a configuration, the intensity of the back-scattered probe light 42 is at a maximum when the depolarization of the probe light 12 at the target location is at a minimum.

Even further alternatively, and as shown in FIGS. 1A, 1B, 2A and 2B, the polarization modulator 30 may be positioned between the target position 210 and the polarization sensitive sensor 40 such that the back-scattered probe light 42 is sensed by the polarization sensitive sensor 40 through polarization modulator 30. In such a configuration, the back-scattered probe light 42 is measured through the same polarization modulator 30 as that used to modulate the probe light 12 during the scanning of the probe light 12 over the predefined range. The polarization sensitive sensor 40 only needs to be sensitive to a single fixed polarization direction to ensure that the correct polarization direction for the measurement of the back-scattered probe light 42 is maintained. While modulating the polarization direction of the probe light 12 over the predefined range during the scanning thereof, the back-scattered probe light 42 will automatically be "de-modulated" before being measured by the polarization sensitive sensor 40.

In the embodiment shown in FIG. 1A, the light source 10 is configured to emit linearly polarized probe light 12 which has a power level significantly below the power level required for the multi-photon ionization process. This scanning of the polarization direction of the probe light 12 enables to probe the target position 210 to find the optimum polarization direction P1 for which the depolarization of the probe light 12 is at a minimum (or for which the intensity of the back-scattered probe light 42 is at a minimum when the polarization direction of the polarization sensitive sensor 40 is perpendicular to the polarization direction of the probe light 12). The use of such a probe light 12 having reduced power also reduces any collateral damage to the skin tissue 200 during the probing of the target position 210 to find the optimum polarization direction P1.

The skin treatment device 100 shown in FIGS. 1A and 1B also comprises the optical system 70. The optical system 70 is configured for focusing light towards the target position 210 inside the skin tissue 200. The optical system 70 is shown in FIGS. 1A and 1B as a single-lens element 70, but may, of course, comprise multiple lens elements (not shown) to focus the light towards the target position 210. The optical system 70 may be arranged downstream of the polarization modulator 30 (as shown in FIGS. 1A and 1B) or, alternatively, the optical system 70 may be arranged upstream of the polarization modulator 30, i.e. between the light source 10 and the polarization modulator 30 (not shown in FIGS. 1A and 1B). The optical system 70 may also comprise multiple lens elements, of which some are arranged upstream of the polarization modulator 30 and some are arranged downstream of the polarization modulator 30 (not shown).

The optical system 70 may further comprise an adjustable lens (not shown) or an adjustable mirror (not shown). Either element, or a combination thereof, can provide the focusing action. Both elements may be adjustable to adjust the position of the focal spot at the target position 210, both in the depth direction with respect to the skin surface and across the skin surface. The adjustable lens may comprise a lens with a distance setting, or may be a zoom lens. The adjustable mirror may comprise a mirror that is rotatable in one or more, for example two, directions. The mirror may be flat, e.g. when combined with a lens, or may be concave, in particular if the mirror provides focusing action.

Advantageously, the adjustable lens comprises an autofocus lens. Such a lens is automatically adjusted with respect to the skin surface. This ensures a correct treatment depth in almost all circumstances.

In FIG. 1A, the light source 10 emits linearly polarized probe light 12 for selecting the optimum polarization direction P1. In FIG. 1B, the light source 10 emits linearly polarized treatment light 22 having an intensity level at or above the intensity level required for multi-photon ionization. The light source 10 may, for example, have an adjustable light output level which may be adjusted to emit either the linearly polarized probe light 12 or the linearly polarized treatment light 22. The polarization modulator 30 which is adjusted, using the probe light 12, to the optimum polarization direction P1, is now used to adapt the polarization direction of the treatment light 22 to the optimum polarization direction P1 and focused into the skin tissue 200 to the target position 210.

During use, an output window (not shown) of the skin treatment device 100 is positioned in close proximity to or in contact with the skin surface of the skin tissue 200 to be treated. Typically, an index-matching fluid may be used between the output window of the skin treatment device 100 and the skin surface to enhance optical coupling of the emitted linearly polarized probe light 12 or treatment light 22 into the skin tissue 200. The skin treatment device 100 is configured to create a focus of the emitted linearly polarized probe light 12 or treatment light 22 at the target position 210. If the skin treatment device 100 is being used to reduce wrinkles in the skin tissue 200, the target position 210 is disposed in the collagen of the dermis in order to create microscopic lesions at the target position 210, which results in new collagen formation.

The invention uses the fact that the skin transmits electromagnetic radiation that is to be focused, in the dermis, to a very small focal spot. To maximize this effect, a wavelength of the light is between 800 and 1100 nm, for example produced by a Nd:YAG laser with emission at 1064 nm and 1-1000 ps pulse duration. In this range, transmission is relatively high and scattering and linear absorption are low. It is however not excluded to use other wavelengths.

In particular, the predetermined pulse time is between 100 ps and 10 ns. In this range, the plasma generated by the multi-photon ionization is very local, i.e. has a small spatial extension, which minimizes the risk of unintended damage to surrounding tissues. Furthermore, the peak power required to obtain multi-photon ionization is substantially independent of the pulse time in this range. However, other pulse times, e.g. in the range of about 100 fs to 100 ps, may also be used, and even in the ns and ms ranges.

Typically, the deliverable energy level in the laser beam pulse is between 0.1 and 10 mJ, measured at the surface of the skin. Such energy levels have turned out to be useful in the treatment, i.e. generate sufficient damage to stimulate new tissue growth. More specifically, the energy level is between about 0.5 and 5 mJ, and typically about 1 mJ. However, other energy levels are not excluded, such as levels up to about 20 mJ for large treatment depths of up to 2 mm. In the above energy level indications, the energy is measured at the surface of the skin, i.e. it relates to the energy actually emitted into the skin.

In all of the above, it is to be understood that instead of a single pulse, it is also possible to provide a number of pulses, as long as the pulses generate a LIOB phenomenon.

As indicated before, the polarization modulator 30 may be disposed in any suitable part of the skin treatment device 100 and integrated, if convenient, with another optical component or even the light source. The polarization modulator 30 may be any suitable optical element known in the art, such as a rotating half-lambda wave plate, electro-optic, acousto-optic modulator.

The skin comprises multiple layers with different optical properties. The epidermis is composed of the outermost layers and forms a waterproof protective barrier. The outermost layer of the epidermis is the stratum corneum which, due to its microscopic fluctuations in roughness, impedes the coupling of light between the skin treatment device 100 and the skin tissue 200. Underneath the epidermis, the dermis is situated. The dermis comprises the collagen fibers at which the skin treatment typically is aimed.

Typically, the skin treatment device 100 has a numerical aperture (NA) of at least 0.2, preferably at least 0.4. Such values for the numerical aperture relate to safety for the overlying skin layers, in particular the epidermis. Since, in particular, the epidermis contains many chromophores such as melanin, the residual linear absorption in the epidermis is not negligible. Therefore, it is advantageous to keep the fluence, or energy density, in such layers sufficiently low. This may be achieved by providing a strongly focused laser beam, i.e. with a large angle of convergence, and hence a large numerical aperture of the optical system. The laser beam then covers a sufficiently large area to maintain the fluence in the epidermis within an acceptable range. In particular, the fluence in the epidermis should be at most 3 J/cm2. Note that the desired numerical aperture depends on the treatment depth and on the actual energy in the pulse. Model calculations show that a numerical aperture of at least 0.4 suffices for a treatment depth of 0.5 mm and an energy of 1 mJ in the plasma (in the focus), while higher NAs are needed for higher energy levels and smaller treatment depths, and vice versa.

Note that the NA needed for large treatment depths is of course smaller than that for small treatment depths, because of the larger distance to the epidermal layers that are not to be damaged. However, the total intensity and energy needed to achieve a sufficient multi-photon ionization at the treatment depth becomes larger, due to residual absorption and scattering in the overlaying layers.

For typical treatment depths, a numerical aperture of at least 0.7 may be advantageous to provide an optimum intensity in the focus, and to minimize the thermal load on the superficial layers of skin.

In particular, a fluence of the laser beam pulse is at the most 3 J/cm2 in the skin between the surface of the skin and the dermis layer. Such a fluence is deemed safe for said skin layers. Together with the preferred energy levels for the laser beam pulse, this leads to preferred laser beam apical angles, in particular of at least 11° (half angle) for 1 mJ and a treatment depth of 0.5 mm. In dependence on the desired treatment depth and pulse energy, the skilled person can easily determine the preferred apical angle, or the related numerical aperture.

Typically, the treatment depth is between 0 and 2 mm, more particularly between 0.2 and 1.5 mm, below the surface of the skin. This is based on a typical total thickness of the epidermis with the stratum corneum, in the face, of between 0.06 and 0.2 mm and a typical thickness of the dermis layer of 2 mm. Hence, the dermis may be found at a depth of between 0.2 and about 2 mm. A treatment depth of between 0.5 and 1.5 mm offers a range that allows treatment of the dermis with sufficient expansion yet without any risk for the surrounding layers such as the epidermis. In particular cases, the epidermis and/or dermis may be thinner or thicker, or may be present at a slightly different depth, such as on other parts of the body, e.g. the hands. In that case, the skilled person will easily be able to determine the depth and/or thickness of the dermis, and configure the device accordingly. A different treatment depth may then be fixed after establishing the depth and thickness of the dermis layer. It is also possible to use or include a device for automatic determination of the thickness of the dermis and/or epidermis, such as an ultrasonographic device, for example the Stiefel Cutech "Dermal depth Detector", or alternatively an OCT device (optical coherence tomography).

Figure 2A:
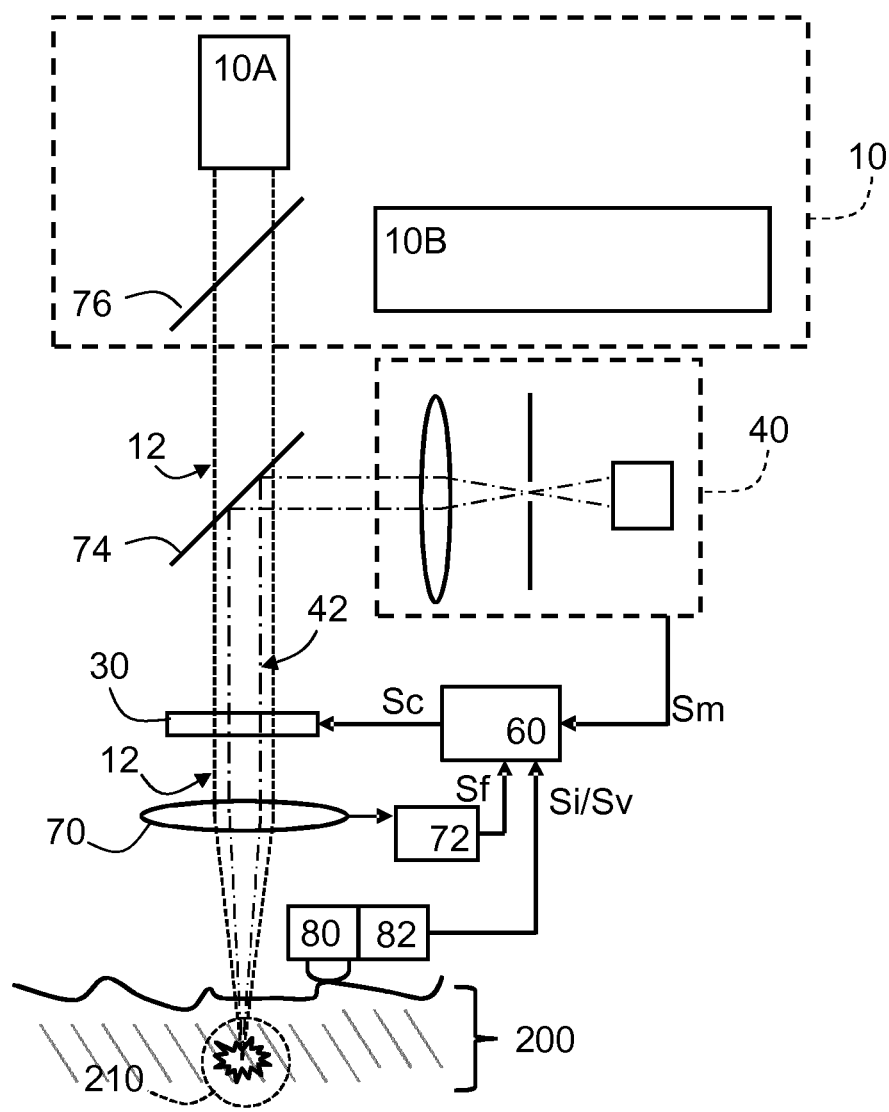
Figure 2B:
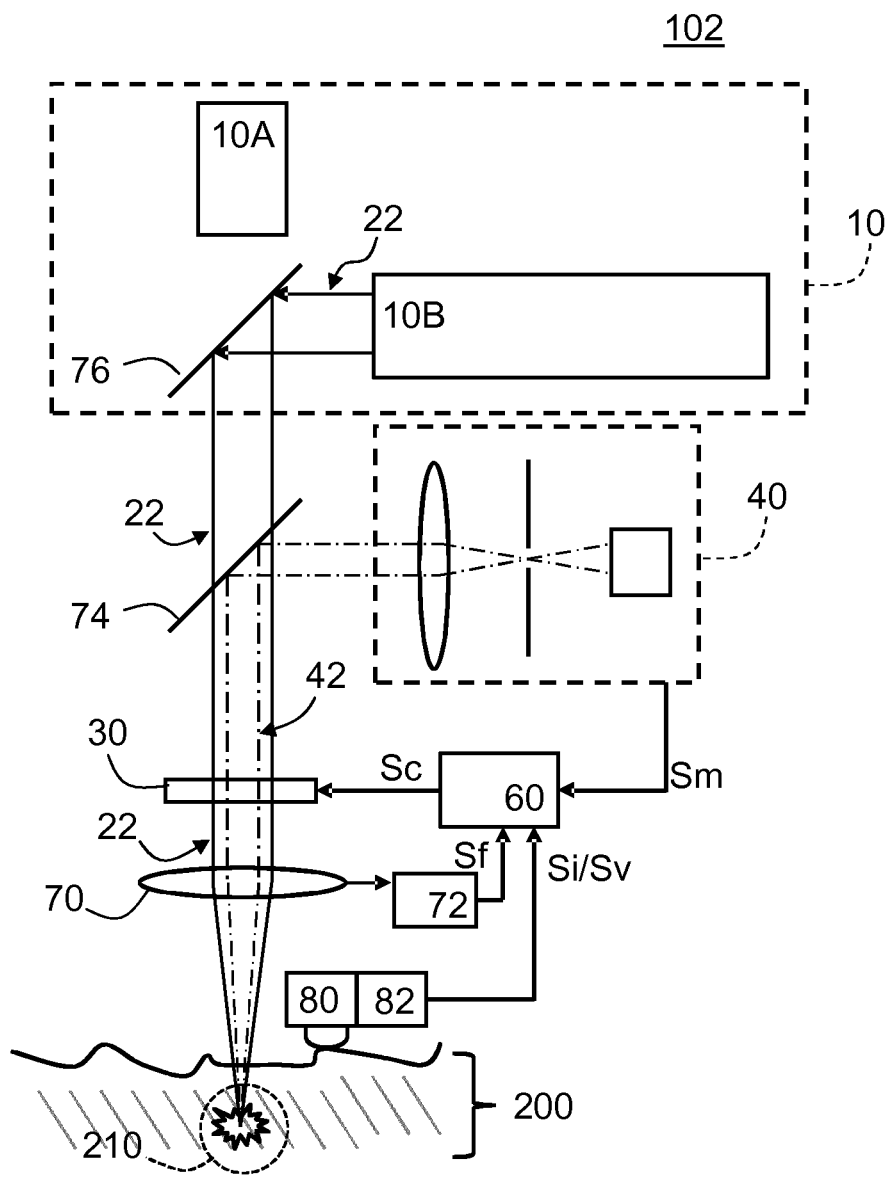

FIGS. 2A and 2B diagrammatically show a second embodiment of the skin treatment device 102 according to the invention. In the embodiment shown in FIGS. 2A and 2B, the polarization modulator 30, the sensor 40, the controller 60 and the optical system 70 are identical to the embodiment shown in FIGS. 1A and 1B. However, in the embodiment shown in FIGS. 2A and 2B, the skin treatment device 102 comprises a light source 10 having a probe light emitter 10A and a separate treatment light emitter 10B. The probe light emitter 10A is configured for generating probe light 12 being linearly polarized light having an intensity level significantly below the intensity level required for generating the multi-photon ionization. The treatment light emitter 10B is configured for generating treatment light 22 being linearly polarized light having an intensity at or above the intensity level required for the multi-photon ionization process. As indicated before, the use of separate light emitters for, on the one hand, the probing and the selection of the optimum polarization direction P1 and, on the other, for the treatment of the skin tissue 200, may reduce the overall cost of the skin treatment device 102. In the embodiment shown in FIGS. 2A and 2B, the light of the probe light emitter 10A and of the treatment light emitter 10B is combined using a further semi-transparent mirror 76.

The embodiment of the skin treatment device 102 shown in FIGS. 2A and 2B further comprises a focus sensor 72 for sensing a depth of the target position 210 at which the optical system 70 focuses the emitted linearly polarized probe light 12 and/or treatment light 22, or for sensing a change in depth of the target position 210. The inventors have found that even a change in depth of the target position 210 may require the skin treatment device 102 according to the invention to re-initiate the scanning of the polarization direction of the probe light 12 over the predefined range for re-selecting the optimum polarization direction P1. The focus sensor 72 is coupled to the controller 60 and provides a focus signal Sf to the controller 60 which is representative of the position of the target position 210 or which is representative of a change in position of the target position 210.

The embodiment of the skin treatment device 102 shown in FIGS. 2A and 2B further comprises a further sensor 82 for sensing the presence of the multi-photon ionization inside the skin tissue 200 when the linearly polarized treatment light 22 is emitted towards the target position 210. The further sensor 82 is coupled to the controller 60 and provides an ionization signal Si to the controller 60 which is representative of the occurrence of the multi-photon ionization process in the skin tissue 200. Such a further sensor 82 may be selected from a list comprising: a photodetector, a grating with a CCD camera and an acoustic sensor.

The embodiment of the skin treatment device 102 may also comprise a motion sensor 80 for sensing motion of the skin treatment device 102 in a direction parallel to the skin surface. The motion sensor 80 may be coupled to the controller 60 and provide a motion signal Sv to the controller. The controller 60 may subsequently be configured to re-adjust the optimum polarization direction P1 in response to a change in position of the skin treatment device 102 along the skin surface. Similar to the change in depth of the target position 200, also a relocation of the skin treatment device 102 along the skin surface may result in a change of the optimum polarization direction for this changed position. So, the controller 60 may be configured to receive a motion signal Sv from the motion sensor 80 and in response thereto the controller 60 may use this motion signal Sv as a trigger to re-initiate the scanning of the polarization direction of the probe light 12 over the predefined range for re-selecting the optimum polarization direction P1 before applying the multi-photon ionization treatment at the relocated target position 210.

The embodiment of the skin treatment device 201 shown in FIG. 2A represents a mode in which the probe light emitter 10A emits probe light 12 for selecting the optimum polarization direction P1. In FIG. 2B, the probe light emitter 10A is switched off and the treatment light emitter 10B is switched on to emit treatment light 22 via the polarization modulator 30 towards the target position 210 to generate multi-photon ionization at the target location 210.

Figure 3:
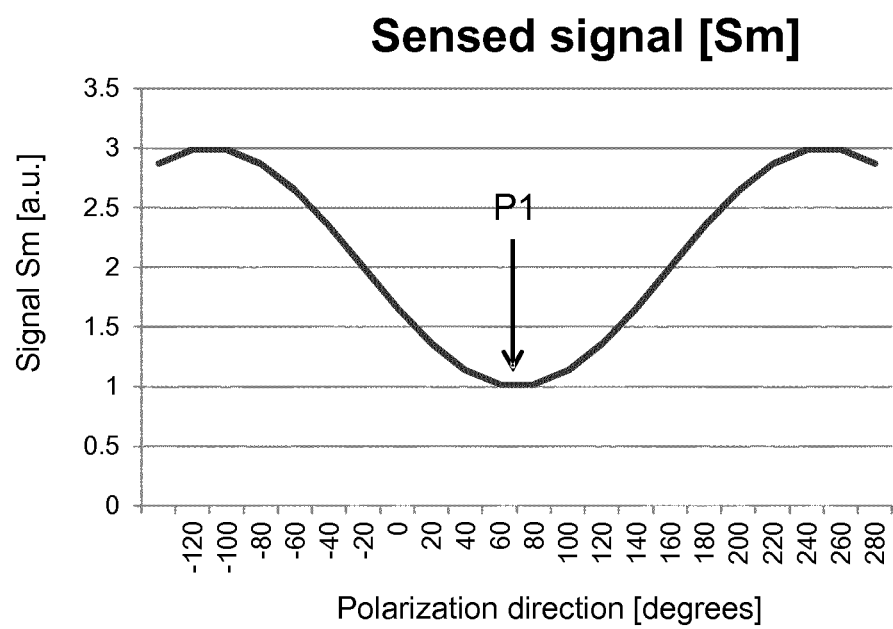

FIG. 3 diagrammatically shows an example of a measurement signal Sm measured by the sensor 40 upon a change of the polarization direction of the emitted linearly polarized probe light 12. In the graph of FIG. 3, the horizontal axis represents the angle of linear polarization of the emitted linearly polarized probe light 12, and the vertical axis represents the sensor signal in arbitrary units. In the current embodiment, the predefined polarization direction of the polarization sensitive sensor 40 is arranged perpendicularly to the polarization direction of the linearly polarized probe light 12. When polarized light enters the skin, it is partially depolarized by scattering effects inside the skin tissue 200 and by the presence of collagen tissue, which changes the polarization of the light. As indicated before, these depolarization effects reduce the number of photons that have the same polarization direction inside the target position. In the known solutions, the power of the treatment light 22 for generating multi-photon ionization at the target position 210 is increased. In the embodiment according to the invention, the back-scattered probe light 42 is sensed. When sensing the back-scattered probe light 42, using the predefined polarization direction perpendicular to the polarization direction of the probe light 12, the sensor 40 only senses a portion of the back-scattered probe light 42 for which the polarization direction is altered due to the depolarization inside the skin tissue 200. As such, when the sensed intensity of the back-scattered probe light 42 in the current configuration is low, also the depolarization, when focusing at the current target position 210, is low. When the depolarizing effect of the skin tissue 200 at the target location 210 is low, the number of photons having the same polarization direction is relatively high, which results in a minimum power of the treatment light 22, which may be sufficient to still generate multi-photon ionization. As indicated before, the inventors have found that this specific polarization direction may differ at different locations on the skin tissue 200 and so the skin treatment device 100, 102 according to the invention comprises the polarization modulator 30 which is configured to locally adapt the polarization direction of the linearly polarized treatment light 22.

Figure 4:
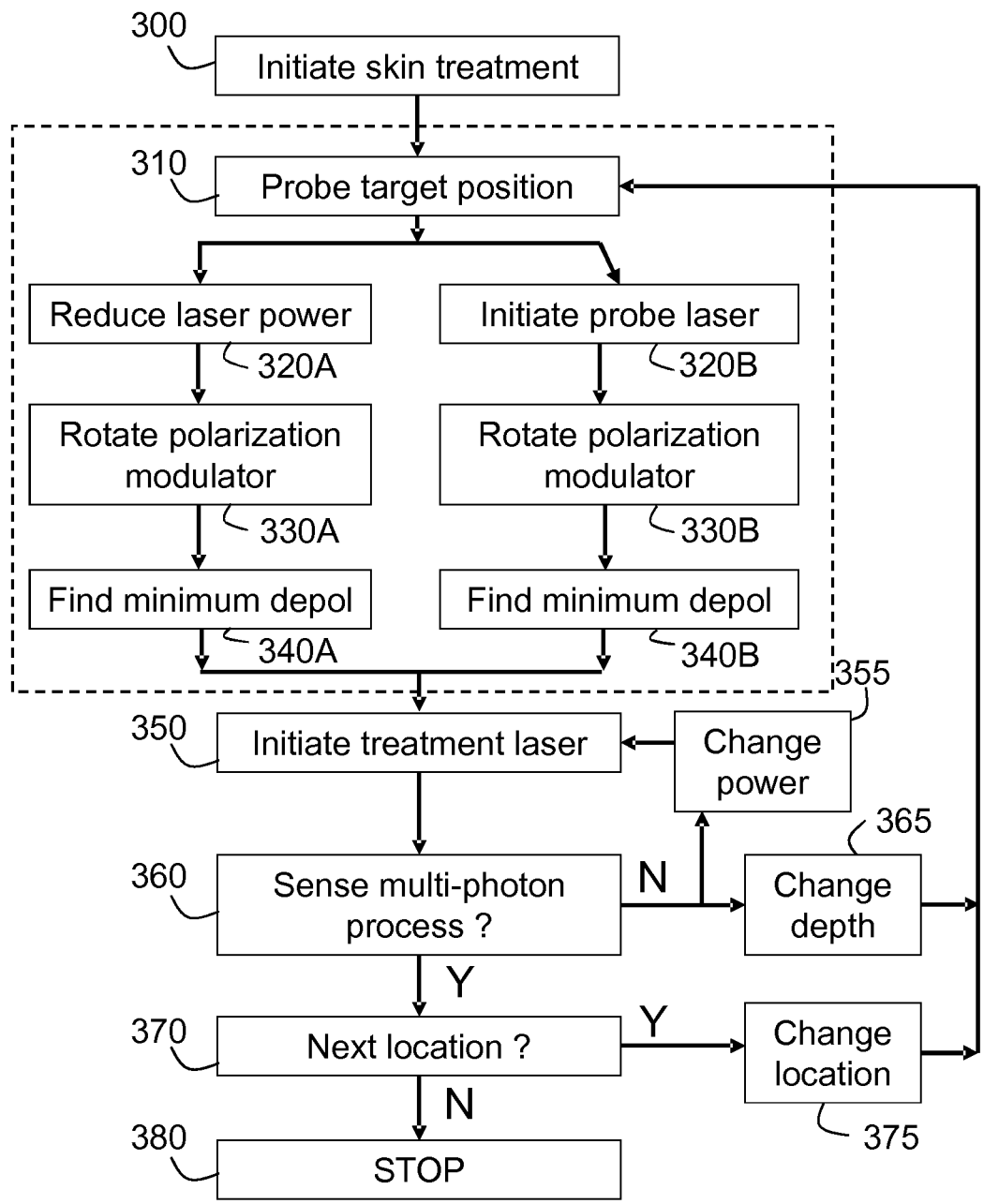
FIG. 4 shows a flow diagram for controlling the skin treatment device according to the invention.

FIG. 4 shows a flow diagram for controlling the skin treatment device 100, 102 according to the invention. This flow diagram may be coded in a computer program product for controlling the skin treatment device 100, 102 according to the invention. The flow diagram starts at step 300 "initiate skin treatment" in which the skin treatment is initiated in a skin treatment device 100, 102. Next, in step 310 "probe target position", the target position is probed to find the optimum polarization direction P1 in which the depolarization of the probe light 12 is at a minimum. Next, the process is split into two flows, one for the embodiment shown in FIGS. 1A and 1B (steps 320A, 330A and 340A) in which the skin treatment device 100 comprises a light source 10, of which the intensity may be changed to generate both the probe light 12 and the treatment light 22, and one for the embodiment shown in FIGS. 2A and 2B (steps 320B, 330B and 340B) in which the skin treatment device 102 comprises separately a probe light emitter 10A and a treatment light emitter 10B. Looking at the flow for the embodiment shown in FIG. 1A, the step 320A "reduce laser power" controls the light source 10 of the skin treatment device 100 to reduce the power to generate the linearly polarized probe light 12, which is significantly below the power necessary to achieve multi-photon ionization. Step 330A "rotate polarization modulator" subsequently scans the polarization direction of the emitted linearly polarized probe light 12 and step 340A "find minimum depol" finds which polarization direction provides a minimum in the depolarization of the probe light 12 i.e. the optimum polarization direction P1. Looking at the flow for the embodiment shown in FIG. 2A, the step 320B "initiate probe laser" controls the probe light emitter 10A of the light source 10 to emit the probe light 12 at a power level significantly below the power necessary to achieve multi-photon ionization. Step 330B "rotate polarization modulator" and step 340B "find minimum depol" are identical to the steps 330A and 340A and subsequently scan the polarization direction of the emitted linearly polarized probe light 12 and find which polarization direction provides a minimum in the depolarization of the probe light 12. Next, in step 350 "initiate treatment laser", the treatment light emitter 10B is initiated, or the intensity level of the light source 10 is increased to a level at or above which multi-photon ionization may occur in the skin tissue 200. Subsequently, in step 360 "sense multi-photon process?" the occurrence of the multi-photon process is sensed. If no multi-photon process is sensed (indicated with "N"), the skin treatment device 100, 102 may either move to step 355 "change power" in which the power of the treatment light 22 is increased, after which the treatment light emitter 10B is re-initiated in step 350. Alternatively, the skin treatment device 100, 102 may change the depth of the target position 210 in step 365 "change depth", after which the process returns to the probing step 310 of the changed target position 210. If, in step 360, the multi-photon process is sensed (indicated with "Y") the process may proceed to step 370 "next location?" in which it is checked whether the skin treatment should continue at a different location. If not (indicated with "N"), the process stops at step 380 "stop". If further locations need to be treated (indicated with "Y"), the process continues with step 375 "change location" in which the location of the skin treatment device 100, 102 is changed relative to the skin surface and again the process returns to the probing step 310 at this changed position.

In summary, the invention provides a non-invasive skin treatment device 100 comprising: a light source 10 constructed and configured for generating linearly polarized probe light 12 and linearly polarized treatment light 22, a polarization modulator 30 constructed and configured for controlling a polarization direction of the probe light and a polarization direction of the treatment light, a polarization sensitive sensor 40 constructed and configured for sensing a level of depolarization of the probe light by sensing an intensity of back-scattered probe light 42 from the target position 210 in a predefined polarization direction of the polarization sensitive sensor, and a controller 60 being configured for scanning the polarization direction of the probe light over a predefined range while receiving the measurement signal Sm and for selecting an optimum polarization P1 direction for which the depolarization of the probe light is at a minimum. The invention further provides a computer program product for controlling the skin treatment device.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A skin treatment device using polarized light to initiate a multi-photon ionization process at a target position in skin tissue, the skin treatment device comprising:
   a light source constructed and configured for generating (i) linearly polarized probe light and (ii) linearly polarized treatment light,
   a polarization modulator constructed and configured for controlling (i) a polarization direction of the probe light and (ii) a polarization direction of the treatment light,
   a polarization sensitive sensor constructed and configured for sensing a level of depolarization of the probe light in the skin tissue as a function of an intensity of back-scattered probe light from the target position at a predefined polarization direction of the polarization sensitive sensor, wherein the polarization sensitive sensor outputs a measurement signal (Sm) indicative of the intensity of back-scattered probe light, and
   a controller, responsive to the measurement signal (Sm) from the polarization sensitive sensor, for controlling, via a control signal (Sc), the polarization modulator and the light source, wherein the controller (i) controls the polarization modulator to scan the polarization direction of the probe light over a predefined range of polarization directions, (ii) selects an optimum polarization (P1) direction from the predefined range of polarization directions for which the level of depolarization of the probe light in the skin tissue is at a minimum, and (iii) further controls the polarization modulator and the light source, responsive to selecting the optimum polarization (P1) direction, to set the selected optimum polarization direction as the polarization direction of the treatment light at the target position for generating the multi-photon ionization process.

2. The skin treatment device according to claim 1, wherein the skin treatment device is configured and constructed to maintain the predefined polarization direction of the polarization sensitive sensor parallel to the polarization direction of the probe light during the scanning of the polarization direction of the probe light, the optimum polarization direction (P1) being selected as the polarization direction of the probe light for which the intensity of the sensed back-scattered probe light is at a maximum seen over the predefined range of polarization directions of the probe light, or wherein the skin treatment device is configured and constructed to maintain the predefined polarization direction of the polarization sensitive sensor perpendicular to the polarization direction of the probe light during the scanning of the polarization direction of the probe light, the optimum polarization direction (P1) being selected as the polarization direction of the probe light for which the intensity of the sensed back-scattered probe light is at a minimum seen over the predefined range of polarization directions of the probe light.

3. The skin treatment device according to claim 2, wherein the polarization modulator is positioned between the target position and the polarization sensitive sensor such that the back-scattered probe light is transmitted to the polarization sensitive sensor via the polarization modulator.

4. The skin treatment device according to claim 1, wherein the skin treatment device comprises an optical system for focusing the probe light and/or the treatment light to the target position inside the skin tissue, and wherein the controller is connected to the optical system and is configured and constructed for re-initiating the scanning of the polarization direction of the probe light over the predefined range for re-selecting the optimum polarization direction (P1) in response to a change in depth of the target position inside the skin tissue relative to a skin surface.

5. The skin treatment device according to claim 1, wherein the controller is connected to a motion sensor for sensing motion of the skin treatment device parallel to the skin surface, and wherein the controller is configured and constructed for re-initiating the scanning of the polarization direction of the probe light over the predefined range for re-selecting the optimum polarization direction (P1) in response to a change in position of the skin treatment device along the skin surface.

6. The skin treatment device according to claim 1, wherein a probe light power level is below a treatment light power level required for the multi-photon process.

7. The skin treatment device according to claim 1, wherein the light source comprises a probe light emitter for generating the linearly polarized probe light, and comprises a treatment light emitter for generating the linearly polarized treatment light.

8. The skin treatment device according to claim 1, wherein the skin treatment device comprises a further sensor for sensing an occurrence of the multi-photon process at the target position, wherein the further sensor is different from the polarization sensitive sensor.

9. The skin treatment device according to claim 8, wherein the controller is connected to the further sensor for sensing the occurrence of the multi-photon process when the target position is exposed to the linearly polarized treatment light, and wherein the controller is configured, when no multi-photon process is sensed, to:
   adjust the power level of the linearly polarized treatment light, or
   reduce a depth of the target position inside the skin tissue relative to the skin surface.

10. The skin treatment device according to claim 9, wherein the further sensor is selected from a list comprising: a photodetector, a grating in combination with a CCD camera, and an acoustic sensor.

11. The skin treatment device according to claim 1, wherein the target position is between 0 and 2 mm below the skin surface, or wherein the target position is between 0.5 and 1.5 mm below the skin surface.

12. A non-transitory computer readable storage medium having stored thereon a computer program product configured for controlling the skin treatment device according to claim 1, wherein the computer program controls the controller of the skin treatment device for performing the steps of:

generating and emitting the linearly polarized probe light towards the target position in skin tissue, using the light source, scanning the polarization direction of the probe light over the predefined range, using the polarization modulator, while receiving a measurement signal (Sm) from the polarization sensitive sensor, and selecting the optimum polarization (P1) direction for which the depolarization of the probe light is at a minimum.

13. The non-transitory computer readable storage medium having stored thereon the computer program product of claim 12, wherein the computer program further controls the controller for performing the steps of:

setting the selected optimum polarization direction (P1) as the polarization direction of the treatment light at the target position, using the polarization modulator, and generating and emitting the linearly polarized treatment light towards the target position, using the light source for generating the multi-photon ionization process.

\* \* \* \* \*